United States Patent [19]

Manghisi et al.

[11] Patent Number: 4,587,242

[45] Date of Patent: May 6, 1986

[54] SULFONIC RESINS HAVING A THERAPEUTICAL ACTIVITY, PREPARATION THEREOF AND PHARMACEUTICAL COMPOSITIONS CONTAINING THEM

[75] Inventors: Elso Manghisi; Giuseppe Cascio, both of Monza, Italy

[73] Assignee: Instituto Lusofarmaco d'Italia S.p.A., Milan, Italy

[21] Appl. No.: 709,081

[22] Filed: Mar. 7, 1985

[30] Foreign Application Priority Data

Mar. 9, 1984 [IT] Italy .................................. 19960 A/84

[51] Int. Cl.$^4$ ...................... A61K 31/55; C07D 281/10
[52] U.S. Cl. ............................... 514/211; 260/239.3 B
[58] Field of Search .................... 260/239.3 B; 514/211

[56] References Cited

U.S. PATENT DOCUMENTS 3,562,257  2/1971  Kugita et al. ................. 260/239.3 B
3,646,008  2/1972  Kugita et al. ................. 260/239.3 B Primary Examiner—Robert T. Bond

[57] ABSTRACT

A pharmaceutical compound characterized by a delayed release of the therapeutically active component, comprising a sulfonic type ion exchange resin and cis($\pm$)-3-acetyloxy-5-[2-(dimethylamino)ethyl]-2,3-dihydro-2-(4-methoxyphenyl)-1,5-benzothiazepin-4(5H)one, or cis($\pm$)-3-hydroxy-5-[2-(dimethylamino)ethyl]-2,3-dihydro-2-(4-methoxyphenyl)-1,5-benzothiazepin-4(5H)one as a therapeutically active compound.

A process for the preparation of the active compound.

A pharmaceutical composition including said active compound, and use of said composition for the prophylaxis and therapy of acute and chronical coronary insufficiency and of arterial hypertension.

14 Claims, No Drawings

SULFONIC RESINS HAVING A THERAPEUTICAL ACTIVITY, PREPARATION THEREOF AND PHARMACEUTICAL COMPOSITIONS CONTAINING THEM

BACKGROUD OF THE INVENTION

1. Field of the Invention

This invention relates to the art of salt forming between therapeutically active pharmaceutical compounds and ion exchange resins.

2. Prior Art

A pharmaceutical compound named cis($\pm$)-3-hydroxy-5-[2-(dimethylamino)ethyl]-2,3-dihydro-2-(4-methoxyphenyl)-1,5-benzothiazepin-4(5H)-one or cis($\pm$)-3-acetyloxy-5-[2-(dimethylamino)ethyl]-2,3-dihydro-2-(4-methoxyphenyl)-1,5-benzothiazepin-4(5H)-one is known, and the optically active isomers thereof are also known, like for instance the dextrorotatory isomer cis-3-acetyloxy-5-[2-(dimethylamino)ethyl]-2,3-dihydro-2-(4-methoxyphenyl)-1,5-benzothiazepin-4(5H)-one, which is also called dilthiazen.

One way to prepare compounds of this class is taught in Japanese Patent Application No. 44-102252 (1969) to Tanabe Pharmaceutical Co., Ltd.

Dilthiazen is usually administered in the form of a soluble salt having a half-life of 3–4 hours when at a therapheutical dosage; repeated administrations are therefore necessary during the day in order to keep adequate blood levels. This drawback is an obstacle to a more wide and extensive use of the compound both because an administration that must be repeated every 3 or 4 hours is impractical, and because each administration is followed by a blood level peak giving rise to undesirable side effects.

We have now surprisingly found that said drawbacks can be overcome by the use of the new orally administered compound whereby release of the therapeutically active component is delayed, said compound comprising a sulfonic type cation exchange resin characterized in that the acid groups of said resin are partly converted to salts of said therapeutically active component selected from cis($\pm$)-3-acetyloxy-5-[2-(dimethylamino)ethyl]-2,3-dihydro-2-(4-methoxyphenyl)-1,5-benzothiazepin-4-(5H)-one, cis($\pm$)-3-hydroxy-5-[2-(dimethylamino)ethyl]-2,3-dihydro-2-(4-methoxyphenyl)-1,5-benzothiazepin-4(5H) one and the optically active isomers thereof.

Dilthiazem is not very stable when in aqueous solution because the position 3 acetyl group shows a tendency to hydrolize.

SUMMARY OF THE INVENTION

We have surprisingly found that hydrolisis of said acetyl group does not occur during reaction with the cation exchange resin when operating under certain solvent, temperature and pH conditions.

Favourable conditions to effect reaction with the resin are the use of an aqueous or alcoholic-aqueous solvent at temperatures of between 0° C. and 25° C. and a pH range of between 5 and 7.

The reaction medium pH can be controlled by the use of buffer solutions of a pH within said range. As a buffer use can be made of inorganic or organic acids, preferably acetic acid according to Walpole (Walpole G.S.J. Chem. Soc., 105, 2501 (1914)), sodium citrate according to Sorensen (Sorensen, S. P. L. Biochem Z., 21, 131 (1909)), or phosphates according to Sorensen (Sorensen, S. P. L., Biochem Z., 22, 352 (1909)).

Cation exchange resins employed are the strongly acidic ones, e.g. the sulfonic resins. The latter, in fact, consent a delayed release of the drug that is not hardly influenced by the pH and therefore remains substantially constant in the whole length of the gastro-intestinal tract.

Sulfonic resins that can be used are sulfonated styrene-divinylbenzene copolymers or sulfonated polystyrene resins cross-linked with divinylbenzene, commercially available under various trade marks, e.g. "Amberlite" (trade mark of Rohm & Haas), "Dovex" (trade mark of Dow Chemical), or "Zeo Karb" (trade mark of Permutit), but it is obvious that other commercially available resins having strongly acidic groups may be suited to prepare the instant products. The invention is not limited to a class of resins of a given cross-linking and particle size.

Especially good results were obtained with "Dovex" resins of the type employed in the experimental section hereinafter.

The invention has more especially as an object the afore defined resins, characterized in that only a part of their acid groups is in the form of salt of the therapeutically active compound, while the remaining acid groups are in the form of alkali or alkaline earth metal salts. By alkali metal it is preferably meant sodium or potassium.

By alkaline earth metal is preferably meant calcium.

Another object of the invention is the previously defined resins, characterized in that they contain from 30 to 60% by weight of the therapeutically active compound, and water buffered by a buffer solution comprising e.g. the above mentioned buffer solutions. Said buffer solution has preferably a pH of between 5 and 7.

Total buffered water remaining enclosed within the resin is in the range of between 7 and 15%, based on the total preparation weight.

More preferably, the employed buffer solution comprises a sodium-buffered citric acid solution of a pH between 6 and 7.

It was found in the practice that presence of the buffer solution within the resin is a critical item.

In fact, only resins containing buffer solution and the active compound of the invention can be stored for the required time.

On the contrary, in the absence of a buffer solution, the moisture in the resin consisting for instance just of distilled water, dilthiazem shows a tendency to degrade on standing and the preparation becomes industrially unpractical.

The new compound is suitably produced through a procedure characterized in that: (a) said resin is contacted, in its acid form, with an alcohol-water solution of said therapeutically active component in its free base form, adopting such a ratio of resin to active component that from 10 to 50% of the resin ionic groups become bound on the form of a salt at a temperature of between 20° and 25° C., said alcohol-water solution including water and an alcohol selected from methanol, ethanol and isopropanol in the ratio of one part of water to three parts of alcohol; (b) the remaining resin acidic groups are converted to salt through reaction with an alkali or alkaline earth metal cation salt; (c) the obtained resin is washed with one of the aforementioned buffer solutions.

Another way to prepare the new invention compound is contacting a sulfonic resin in its alkali or alkaline earth metal salt form with a salt of the therapeutically active compound in a buffered aqueous solution.

Besides, the new compound can be suitably obtained by reacting a sulfonic resin (whose acid groups have been converted to the form of salts of cis(+)-3-hydroxy-5-[2-(dimethylamino)ethyl]-2,3-dihydro-2-(4-methoxyphenyl)-1,5-benzothiazepin-4(5H)-one, and possibly also salts of an alkali or alkaline earth metal) with acetic acid anhydride or other acetic acid derivative at a temperature of between room temperature and 80° C., finally washing the resin with one of the aforementioned buffer solutions.

DETAILED DESCRIPTION OF THE PREFERRED EMBODIMENTS

The new compound (dilthiazem resinate) has a gradual release in the intestine achieving the gradual onset of the pharmacological effects which further are long lasting. This is confirmed by the coronaro-dilating activity (inhibition of coronar artery spasm induced by vasopression "P" in Guines pigs, Table 1). Further dilthiazem resinate has a toxycity which is decidedly lower than dilthiazem chlorhydrate (Table 2).

TABLE 1

Behaviour of vasopressing (P) induced ECG modifications (1 UI/kg i.v. in 5 sec.) in Guinea pigs treated or not by gavage by 5 mg/kg dilthiazem chlorhydrate or by the equivalent dose of resinate.

| Number of animals | Treatment 5 mg/kg | % of animals having coronar artery spasm | % of animals having rhythm alterations (extrasystoles) |
|---|---|---|---|
| 10 | P | 100 | 100 |
| 10 | Dilthiazem chlorhydrate 10 min before P | 40 | 40 |
| 10 | Dilthiazem chlorhydrate 30 min before P | 40 | 40 |
| 10 | Dilthiazem chlorhydrate 90 min before P | 50 | 50 |
| 10 | Dilthiazem chlorhydrate 180 min before P | 60 | 60 |
| 10 | Dilthiazem chlorhydrate 360 min before P | 100 | 100 |
| 10 | P | 100 | 100 |
| 10 | Dilthiazem resinate 10 min before P | 50 | 50 |
| 10 | Dilthiazem resinate 30 min before P | 50 | 50 |
| 10 | Dilthiazem resinate 90 min before P | 40 | 40 |
| 10 | Dilthiazem resinate 180 min before P | 40 | 40 |
| 10 | Dilthiazem resinate 360 min before P | 50 | 50 |

TABLE 2

$DL_{50}$* of dilthiazem resinate (A)** and of dilthiazem chlorhydrate (B) at the 7th day of treatment

| Animal species | Sex | Treatment | $DL_{50}$ at the 7th day of treatment mg/kg |
|---|---|---|---|
| Rat | M | A os | 1600 |
| Rat | F | A os | 1600 |
| Rat | M | B os | 688.7 |
| Rat | F | B os | 688.7 |
| Mus musculus | M | A os | 1600 |
| Mus musculus | F | A os | 1600 |
| Mus musculus | M | B os | 619.8 |
| Mus musculus | F | B os | 619.8 |

*Determined according to the method of probits by Finney
**The dilthiazem resinate dose is expressed by the equivalent by weight of dilthiazem chlorhydrate.

This invention has also as an object pharmaceutical compositions containing at least one of the aforementioned drugs as an active principle. These compositions are preferably intended for oral use and can be in the form of powders, tablets, coated tablets, cachets, capsules, granules, emulsions or syrups.

EXAMPLE 1

Mixed resin salt of sodium and cis(+)-3-acetyloxy-5-[2-(dimethylamino)ethyl]-2,3-dihydro-2-(4-methoxyphenyl) 1,5-benzothiazepin-4(5H)-one (dilthiazem).

One hundred thirty nine grams of "Dowex 50W-X4 ($H^+$)" resin having a moisture content of 64% by weight, 50 grams dilthiazem in the free base form, and a mixture of 600 mg alcohol and 200 ml water are stirred at 20°-25° C. for approximately 5 hours.

The resin is then recovered by filtration and a 2% $NaHCO_3$ aqueous solution is added twice thereto with shaking. The resin is again recovered by filtration, washed with a pH 5 acetic acid buffer solution and allowed to dry in the air until its moisture content is down to approximately 10%.

The recovered resin weights 112 grams and contains 40% by weight dilthiazem (figured as the hydrochloride).

In a similar way the following resin salts are prepared:
mixed sodium and cis(−)-3-acetyloxy-5-[2(dimethylamino)ethyl]-2,3-dihydro-2-(4-methoxyphenyl)-1,5-benzothiazepin-4(5H)-one salt,
mixed sodium and cis(+)-3-acetyloxy-5-[2-(dimethylamino(ethyl]-2,3-dihydro-2-(4-methoxyphenyl)-1,5-benzothiazepin-4(5H)-one salt,
mixed potassium and cis(+)-3-hydroxy-5-[2-(dimethylamino)ethyl]-2,3-dihydro-2-(4-methoxyphenyl)-1,5-benzothiazepin-4(5H)-one (deacetyldilthiazem) salt,
mixed potassium and cis(±)-3-hydroxy-5-[2-(dimethylamino)ethyl]-2,3-dihydro-2-(4-methoxyphenyl)-1,5-benzothiazepin-4(5H)-one salt.

The following table 3 shows dilthiazem percentages released to simulating buffer solutions (simulating gastric juice and intestinal juice in the absence of enzymes) by 100 mg of a resinate containing 37,5 mg of dilthiazem (figured as the base). Tests were carried with the aid of a MLI-50 rotary thermostatic agitator of Buhler Company set at 37±0.5° C., in 70 ml tubes, introducing 50 ml of buffer to each stage and decanting the suspension after elapse of the established time.

The amount of dissolved dilthiazem was determined through UV absorption values at 236 nm and released dilthiazem percentages refer to dilthiazem present in the resinate.

Buffers preparation:

Solution (A): 8 g monobasic sodium phosphate are dissolved in 1,000 cc water.

Solution (B): 9.47 g dibasic sodium phosphate are dissolved in 1,000 cc water.

pH 1.2 buffer: 4 g NaCl and 176 cc 0.5N HCl are taken to volume with 1,000 cc water. pH is checked and adjusted with dilute HCl.

pH 7.0 buffer: 4.6 g NaCl are added to a mixture of 400 cc solution (A) and 600 cc solution (B). pH is checked and adjusted with NaOH or $H_3PO_4$.

pH 7.4 buffer: 4.4 g NaCl are added to a mixture of 200 cc solution (A) and 800 cc solution (B). pH is checked and adjusted with one of the two solutions.

TABLE 3

| Stage | Simulating buffer pH | Contact time (min) | Released dilthiazem, mg | % released |
|---|---|---|---|---|
| 1 | 1.2 | 60 | 8.45 | 22.45 |
| 2 | 1.2 | 60 | 5.29 | 14.12 |
| 3 | 7.0 | 90 | 6.40 | 17.08 |
| 4 | 7.4 | 90 | 4.41 | 11.77 |
| 5 | 7.4 | 120 | 3.85 | 10.26 |
| dilthiazem released at pH 1.2 | | | 36.57% in 2 hours | |
| dilthiazem released at pH 7.0 | | | 17.08% in 1 and ½ hours. | |
| dilthiazem released at pH 7.4 | | | 22.03% in 3 and ½ hours | |
| Total dilthiazem released | | | 75.68% in 7 hours. | |

EXAMPLE 2

Mixed sodium and cis(+)-3-acetyloxy-5-[2-(dimethylamino)ethyl]-2,3-dihydro-2-(4-methoxyphenyl)-1,5-benzothiazepin-4(5H)-one (resin dilthiazen) salt.

A mixture containing 157 g of "Dowex 50W-X4 (Na+) resin having a moisture content of about 65%, 1,000 cc of pH 5 acetic acid buffer solution according to Walpole, and 50 g dilthiazem hydrochloride is shaken for 55 hrs at 20°-25° C. The mixture is filtered and dried in the air until its moisture content, in the form of a buffered solution, is down to about 10%.

The recovered resin salt weights approximately 90 g and has a dilthiazem content (figured as the hydrochloride) of about 33% by weight.

EXAMPLE 3

Sodium and cis(+)-acetoloxy-5-[2-(dimethylamino)ethyl[-2,3-dihydro-2-(4-methoxyphenyl)-1,5-benzothiazepin-4(5H)-one mixed salt.

Fourteen grams of "Dowex 50W-X4 (H+)" resin having a moisture content of 64% by weight, 5 g of cis(+)-3-hydroxy-5-[2-(dimethylamino)ethyl]-2,3-dihydro-2-(4-methoxyphenyl)-1,5-benzothiazepin-4(5H)-one, and a mixture of 60 ml alcohol and 20 ml water are kept under stirring at 20°-25° C. for approximately 12 hours.

The resin is then recovered by filtration and 30 cc of a 2% $NaHCO_3$ solution is added twice under stirring.

The resin is again recovered by filtration and allowed to dry for 2 days at 60° C. 5 g of the thus prepared resin are reacted with 20 cc acetic acid anhydride in a closed tube at 50° C. for about 200 hours.

The resin is once more recovered by filtration, washed repeatedly with a Sorensen pH 6.4 sodium citrate solution and allowed to dry in the air until its moisture content is down to about 10%.

The recovered resin contains 50.5% by weight dilthiazem (figured as the hydrochloride).

EXAMPLE 4

The following are examples of pharmaceutical preparations:

(a) hard gelatin capsules containing 125 mg of mixed sodium and dilthiazem resin salt.

(b) hard gelatin capsules containing 100 mg of mixed potassium and diacetyldithiazem resin salt.

(c) hard gelatin capsules containing 100 mg of mixed sodium and dilthiazem resin salt, and 25 mg of mixed sodium and diacetyldithiazem resin salt.

We claim:

1. A new orally administrable pharmaceutical compound consenting delayed release of the therapeutically active component, comprising a cation exchange sulfonic type resin, wherein the acid groups of said resin are partly combined in the form of salts of said therapeutically active component selected from cis(±)-3-acetyloxy-5-[2-(dimethylamino)ethyl]-2,3-dihydro-2-(4-methoxyphenyl)-1,5-benzothiazepin-4(5H)-one, cis (±)-3-hydroxy-5-[2-(dimethylamino)ethyl]-2,3-dihydro-2-(4-methoxyphenyl)-1,5-benzothiazepin-4(5H)-one and the optically active isomers thereof.

2. A pharmaceutical compound according to claim 1, comprising from 30 to 60% by weight of said therapeutically active component, based on the weight of the product.

3. A compound according to claim 1 or 2, wherein said resin is selected from sulfonated styrene-divinylbenzene copolymers and sulfonated divinylbenzene-crosslinked polystyrenes.

4. A compound according to claim 3 wherein the resin acid groups that have not been converted to salts of the therapeutically active component are in the form of salts of alkali metals such as sodium or potassium or of alkaline earth metals such as calcium.

5. A compound according to claim 4 characterized in that the therapeutically active component is cis(+)-3-acetyloxy-5-[2-(dimethylamino)ethyl]-2,3-dihydro-2-(4-methoxyphenyl)-1,5-benzothiazepin-4(5H)-one and the metal is preferably sodium or potassium.

6. A compound according to claim 4, wherein the therapeutically active component is cis(+)-3-hydroxy-5-[2-(dimethylamino)ethyl]-2,3-dihydro-2-(4-methoxyphenyl)-1,5-benzothiazepin-4(5H)-one and the metal is preferably sodium or potassium.

7. A new orally administrable pharmaceutical compound consenting delayed release of the therapeutically active component, comprising a cation exchange sulfonic type resin, wherein the acid groups of said resin are partly combined in the form of salts of said therapeutically active component selected from cis(±)-3-acetyloxy-5-[2-(dimethylamino)ethyl]-2,3-dihydro-2-(4-methoxyphenyl)-1,5-benzothiazepin-4(5H)-one, cis(±)-3-hydroxy-5-[2-(dimethylamino)ethyl]-2,3-dihydro-2-(4-methoxyphenyl)-1,5-benzothiazepin-4(5H)-one and the optically active isomers thereof, said compound comprises water that is buffered by means of a buffered solution to a pH of between 5 and 7.

8. A compound according to claim 7, wherein said buffer solution comprises a buffered acid selected from acetic, citric and phosphoric acid.

9. A compound according to claim 8, wherein said buffer solution comprises sodium-buffered citric acid having a pH of between 6 and 7, said buffered solution representing from 7 to 15% by weight of the whole compound.

10. A process for the preparation of a new orally administrable pharmaceutical compound consenting delayed release of the therapeutically active component, comprising a cation exchange sulfonic type resin, where in the acid groups of said resin are partly combined in the form of salts of said therapeutically active component selected from cis($\pm$)-3-acetyloxy-5-[2-(dimethylamino)ethyl]-2,3-dihydro-2-(4-methoxyphenyl)-1,5-benzothiazepin-4(5H)-one, cis($\pm$)-3-hydroxy-5-[2-(dimethylamino)ethyl]-2,3-dihydro-2-(4-methoxyphenyl)-1,5-benzothiazepin-4(5H)-one and the optically active isomers thereof, wherein the process comprises the following steps:

(a) said resin is contacted, in its acid form, with an alcohol-water solution of said therapeutically active component in its free base form, adopting such a ratio of resin to active component that from 10 to 50% of the resin cationic groups become bound in the form of a salt at a temperature of between 20° and 25° C., said alcohol-water solution including water and an alcohol selected from methanol, ethanol and isopropanol in the ratio of one part of water to three parts of the alcohol;

(b) the remaining resin acid groups are converted to salt through reaction with an alkali or alkaline earth metal cation salt;

(c) the obtained resin is washed with said buffer solution.

11. A process for the preparation of a pharmaceutical compound according to claim 10, wherein said resin (whose acid groups have been previously converted to the alkali or alkaline earth metal salt form) is contacted with a buffered aqueous solution of the therapeutically active component.

12. A process for the preparation of a pharmaceutical compound according to claim 10, wherein said resin (the acid groups of which have been converted to the form of salts of cis(+)-3-hydroxy-5-[2-(dimethylamino)ethyl]-2,3-dihydro-2-(4-methoxyphenyl)-1,5-benzothiazepin-4(5H)-one and possibly also salts an alkali or alkaline earth metal) is reacted with acetic acid anhydride at a temperature of between room temperature and 80° C., finally washing the resin with said buffer solution.

13. A pharmaceutical composition comprising a compound according to claim 7, wherein one or more pharmaceutically acceptable carriers are included therein.

14. The use of a compound according to claim 7, for the prohylaxis and therapy of acute and chronical coronary insufficiency and of arterial hypertension, wherein said compound is administered in a daily dose of between 1 and 30 mg per kg of body weight.

* * * * *